United States Patent [19]

Sedlacek et al.

[11] Patent Number: 5,830,880
[45] Date of Patent: Nov. 3, 1998

[54] GENE THERAPY OF TUMORS WITH AN ENDOTHELIAL CELL-SPECIFIC, CELL CYCLE-DEPENDENT ACTIVE COMPOUND

[75] Inventors: Hans-Harald Sedlacek; Klaus Bosslet; Rolf Müller, all of Marburg, Germany

[73] Assignee: Hoechst Aktiengesellschaft, Frankfurt am Main, Germany

[21] Appl. No.: 793,107

[22] PCT Filed: Aug. 25, 1995

[86] PCT No.: PCT/EP95/03370

§ 371 Date: Apr. 18, 1997

§ 102(e) Date: Apr. 18, 1997

[87] PCT Pub. No.: WO96/06940

PCT Pub. Date: Mar. 7, 1996

[30] Foreign Application Priority Data

Aug. 26, 1994 [GB] United Kingdom .................. 9417366
Mar. 29, 1995 [GB] United Kingdom .................. 9506466

[51] Int. Cl.[6] .......................... A61K 48/00; C12N 15/00; C07H 21/04
[52] U.S. Cl. ................. 514/44; 435/320.1; 424/93.2; 424/450; 536/24.1; 935/36
[58] Field of Search ...................... 514/44; 435/320.1; 536/23.1, 23.5, 24.1; 935/36; 424/93.2, 450

[56] References Cited

FOREIGN PATENT DOCUMENTS

93/10135  5/1993  WIPO .
93/13807  7/1993  WIPO .
94/29469  12/1994  WIPO .

OTHER PUBLICATIONS

Haddada et al (1993) Hum. Gene Therapy 4: 703–711.
El–Deiry et al (1993) Cell 75: 817–825.
Culver et al (1992) Science 256: 1550–1552.
Wood et al (1991) Proc. Natl. Acad. Sci. USA 88: 8006–8010.
Miller et al (1995) FASEB J. 9: 190–199.
Marshall, E. (1995) Science 269: 1050–1055.
Crystal, R.G. (1995) Science 270: 404–1410.
Takahashi et al (1992) Cancer Res. 52: 2340–2343.
Matuyama et al (1990) Proc. Natl. Acad. Sci. USA 87: 5744–5748.
Winter et al (1991) Nature 349: 293–299.
Hamel et al (1992) Mol. Cell. Biol. 12: 3431–3438.

Primary Examiner—Bruce R. Campbell
Attorney, Agent, or Firm—Foley & Lardner

[57] ABSTRACT

A DNA sequence for the gene therapy of tumors is described. In its essential elements, the DNA sequence is composed of an activator sequence, a promoter module and a gene for the active substance. The activator sequence is activated, in a cell-specific manner, in proliferating endothelial cells or in cells which are adjacent to these endothelial cells. This activation is regulated by the promoter module in a cell cycle-specific manner. The active substance is an inhibitor of angiogenesis or a cytostatic or cytotoxic molecule. The DNA sequence is inserted into a viral or non-viral vector which is supplemented with a ligand which possesses affinity for the activated endothelial cell.

52 Claims, 7 Drawing Sheets

MULTIPLE NON-SPECIFIC ENHANCER ELEMENTS

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

GCGCGCGGAG ATTGGCTGAC G                                              2 1

( 2 ) INFORMATION FOR SEQ ID NO:2:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:2:

GGCGAGCGGG GATAGGT                                                                                        17

( 2 ) INFORMATION FOR SEQ ID NO:3:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:3:

CTGGGGTCTG ATTGGCTGCT T                                                                                   21

( 2 ) INFORMATION FOR SEQ ID NO:4:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:4:

CGGGCTACCC GATTGGT                                                                                        17

( 2 ) INFORMATION FOR SEQ ID NO:5:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:5:

CTGTCGCCTT GAATGACGTC A                                                                                   21

( 2 ) INFORMATION FOR SEQ ID NO:6:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:6:

CGAGCGCTTT CATTGGT                                                                                        17

( 2 ) INFORMATION FOR SEQ ID NO:7:

( i ) SEQUENCE CHARACTERISTICS:
            ( A ) LENGTH: 375 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:7:

TTCGTGGGGC TGAGGGAACG AGGAAAACAG AAAGGGTGTG GAGATTGGTG AGAGGGAGAG                                          60

CCAATGATGC GCCAGGCTCC CCGTGAGGCG GAGCTTACCC CGCAGCCTGC CTAACGCTGG                                         120

TGGGCCAAAC ACTATCCTGC TCTGGCTATG GGCGGGGCA AGTCTTACCA TTTCCAGAGC                                          180

AAGCACACGC CCCCAGGTGA TCTGCGAGCC CAACGATAGG CCATGAGGCC CTGGGCGCGC                                         240

-continued

```
GCGCGGAGAT  TGGCTGACGC  AGCTTAGAGG  CGAGCGGGGA  TAGGTTACTG  GGCTGGCGGA      300

AGGTTTGAAT  GGTCAACGCC  TGCGGCTGTT  GATATTCTTG  CTCAGAGGCC  GTAACTTTGG      360

CCTTCTGCTC  AGGGA                                                           375
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( x i ) SEQUENCE DESCRIPTION: SEQ ID NO:8:

```
Met  Gly  Trp  Ser  Cys  Ile  Ile  Leu  Phe  Leu  Val  Ala  Thr  Ala  Thr
 1                   5                        10                       15
```

GENE THERAPY OF TUMORS WITH AN ENDOTHELIAL CELL-SPECIFIC, CELL CYCLE-DEPENDENT ACTIVE COMPOUND

TECHNICAL FIELD

A DNA sequence for the gene therapy of tumors is described. In its essential elements, the DNA sequence is composed of an activator sequence, a promoter module and a gene for the active substance.

The activator sequence is activated, in a cell-specific manner, in proliferating endothelial cells or cells which are adjacent to these endothelial cells.

This activation is regulated in a cell cycle-specific manner by the promoter module.

The active substance is an inhibitor of angiogenesis or a cytostatic or cytotoxic molecule. The DNA sequence is inserted into a viral or non-viral vector which is supplemented with a ligand which has affinity for the activated endothelial cell.

1. Tumor Growth and Angiogenesis

The deficient activity of many antitumoral active compounds can be explained, at least to some degree, by the fact that the tumor cells within a tumor node are inaccessible to the antitumoral, in particular high molecular weight, active compounds (Burrows et al., Pharm. Ther. 64, 155 (1994), Baxter et al., Microvasc. Rex. 41, 5 (1991)). Such active compounds have to diffuse through the vascular endothelium and the basal membrane, and through the tumor stroma and tumor parenchyma, in order to reach each individual tumor cell. The extent of this diffusion is essentially determined by the concentration or the concentration gradient of the active compound and its physicochemical characteristics. Moreover, convection, which is directed outwards by the higher pressure in the interior of the tumor (Burrows et al., Microvasc. Res. 41, 5 (1991)), runs counter to the diffusion.

Since tumor blood vessels are accessible even to high molecular weight active compounds, it was consequently proposed at an early stage (Denekamp, Prog. Appl. Microcirc. 4, 28 1984), Denekamp, Cancer Topics 6, 6 1986), Denekamp, Cancer Metast. Rev. 9, 267 (1990), Denekamp, Brit. J. Radiol. 66, 181 (1993)), that use be made of the angiogenesis which is induced by tumors for tumor therapy.

Thus, attempts were made to inhibit tumor growth using substances which inhibit angiogenesis (Bicknell et al., Semin. Cancer Biol. 3, 399 (1992)). Experimental investigations in animals demonstrated that systemic administration of substances which inhibit angiogenesis can also inhibit tumor proliferation. This applies, for example, to suramin (Gagliardi et al., Cancer Rex. 52, 5073 (1992)), to heparin/steroid conjugates (Thorpe et al., Cancer Res. 53, 3000 (1993)), to O-(chloroacetylcarbamoyl)fumigillol (Yamaoka et al., Cancer Res. 53, 4262 (1993)), to monoclonal antibodies against angiogenin (Olson et al., Cancer Res. 54, 4576 (1994)) and to angiostatin (O'Reilly et al., Cell 79, 315 (1994)).

However, the abovementioned methods suffered from the disadvantages of the systemic, non-tumor-specific effect of the angiogenesis inhibitors, their side effects and the risk of fresh tumor growth occurring once the therapy was discontinued.

As an alternative, the idea was conceived of inhibiting the blood supply of the tumors by damaging endothelial cells so that the tumors necrose (Denekamp, Brit. J. Radiol. 66, 181 (1993)). With this idea in mind, the administration was proposed of toxins, cytostatic agents or isotopes which were coupled to antibodies. These antibodies would be specific for the tumor-associated vascular endothelium. The intention was that the antibody conjugates would destroy the tumor-associated blood vessel in an endothelium-specific manner and thereby induce necrosis of the tumor (Burrows et al., Pharma Ther. 64, 155 (1994)).

A further suggestion was to bind thrombogenic substances, cytokines or chemokines to tumor-associated endothelial cells by way of specific antibodies and to exert an influence on tumor growth by way of the blood coagulation, inflammation or immunoregulation which was elicited thereby. Similar effects were sought by the proposal to introduce DNA into endothelial cells by way of endothelial cell-specific antibodies with the DNA transducing the endothelial cells to secrete inflammatory or immunoregulatory substances or substances which affected the growth of tumor cells (Burrows et al., Pharmac. Ther. 64, 155 (1994)).

Membrane antigens on the surface of endothelial cells were proposed as antigens for antibodies of this nature. These antigens include, for example, endoglin, endosialin, p96 dimer, VEGF receptors, PDGF receptors, urokinase (uPA) receptors and various adhesion molecules (Burrows et al., Pharmac. Ther. 64, 155 (1994)).

However, a feature possessed by all these membrane antigens is that they are also present on non-proliferating endothelial cells, at least in relatively low concentrations. Since non-proliferating endothelial cells far outnumber proliferating endothelial cells even in a tumor-affected organism, this does not then adequately ensure the requisite tumor specificity of the effect which is sought by administering the antibody conjugate.

2. Description of the Active Compound

The present invention now relates to an active compound (i.e. a pharmaceutical) which can be given to tumor patients both locally and systemically and which results, at the site of the tumor growth, predominantly if not exclusively in the proliferating endothelial cells and over a relatively long period of time, in angiogenesis being inhibited, in an inflammation being induced or in cytostatic substances being generated directly or indirectly, thereby inhibiting growth of the tumor.

The central component of this active compound is a DNA construct which is composed of the following elements:

(Throughout the text of this application, DNA is used as a common term both for a complementary (cDNA) and a genomic DNA sequence).

2.1 Choice of the Activator Sequence

An activator sequence is to be understood to be a nucleotide sequence (promoter sequence or enhancer sequence) with which transcription factors interact which are formed or are active either in endothelial cells or else in cells which are in the immediate vicinity of proliferating endothelial cells.

a) Activator sequences which are activated in endothelial cells

The CMV enhancer, the CMV promoter (EP 0173.177.B1), the SV40 promoter, or any other promoter sequence or enhancer sequence which is known to the skilled person, may be used as the activator sequence.

However, within the meaning of this invention, the preferred activator sequences include those gene-regulatory sequences or elements from genes which encode proteins which can be detected, in particular, in endothelial cells (or else in cells in the immediate vicinity of proliferating endothelial cells).

Some of these proteins have been described by Burrows et al. (Pharmac. Therp. 64, 155 (1994)) and Plate et al. (Brain Pathol. 4, 207 (1994)). Particular examples of these endothelial cell-specific proteins are:

brain-specific, endothelial glucose-1-transporter
Endothelial cells of the brain are notable for very strong expression of this transporter for the purpose of effecting transendothelial transport of D-glucose into the brain (Gerhart et al., J. Neurosci. Res. 22, 464 (1989)). The promoter sequence has been described by Murakami et al. (J. Biol. Chem. 267, 9300 (1992)).

endoglin
Endoglin appears to be a non-signal transmitting receptor of TGFβ (Gougos et al., J. Biol. Chem. 265, 8361 (1990), Cheifetz, J. Biol. Chem. 267, 19027 (1992), Moren et al., BBRC 189, 356 (1992)). While it is present in low quantities on normal endothelium, it is expressed to an increased extent on proliferating endothelium (Westphal et al., J. Invest. Derm. 100, 27 (1993), Burrows et al., Pharmac. Ther. 64, 155 (1994)). The promoter sequence has been described by Bellon et al. (Eur. J. Immunol. 23, 2340 (1993)) and Ge et al. (Gene 138, 201 (1994)).

VEGF receptors
Two receptors are distinguished (Plate et al., Int. J. Cancer 59, 520 (1994)):
VEGF receptor 1 (flt-1) (de Vries et al., Science 255, 989 (1992) (contains an fms-like tyrosine kinase in the cytoplasmic moiety) and the
VEGF receptor 2 (flk-1, KDR) (Terman et al., BBRC 187, 1579 (1992)) (contains a tyrosine kinase in the cytoplasmic moiety).

Both receptors are to be found almost exclusively on endothelial cells (Senger et al., Cancer Metast. Rev. 12, 303 (1993)).

other endothelium-specific receptor tyrosine kinases
til-1 or til-2 (Partanen et al., Mol. Cell Biol. 12, 1698 (1992), Schnürch and Risau, Development 119, 957 (1993), Dumont et al., Oncogene 7, 1471 (1992))
B61 receptor (Eck receptor) (Bartley et al., Nature 368, 558 (1994), Pandey et al., Science 268, 567 (1995), van der Geer et al., Ann. Rev. Cell Biol. 10, 251 (1994))

B61
The B61 molecule represents the ligand for the B61 receptor. (Holzman et al., J. Am. Soc. Nephrol. 4, 466 (1993), Bartley et al., Nature 368, 558 (1994))

endothelin, especially
endothelin, B (Oreilly et al., J. Cardiovasc. Pharm. 22, 18 (1993), Benatti et al., J. Clin. Invest. 91, 1149 (1993), O'Reilly et al., BBRC 193, 834 (1993). The promoter sequence has been described by Benatti et al., J. Clin. Invest. 91, 1149 (1993).
endothelin 1 (Yanasigawa et al., Nature 332, 411 (1988). The promoter sequence has been described by Wilson et al., Mol. Cell. Biol. 10, 4654 (1990).
endothelin receptors, in particular the endothelin B receptor (Webb et al., Mol. Pharmacol. 47, 730 (1995), Haendler et al., J. Cardiovasc. Pharm. 20, 1 (1992)).

mannose-6-phosphate receptors (Perales et al., Eur. J. Biochem. 226, 225 (1994). The promoter sequences have been described by Ludwig et al. (Gene 142, 311 (1994)), Oshima et al. (J. Biol. Chem. 263, 2553 (1988)) and Pohlmann et al. (PNAS USA 84, 5575 (1987)).

von Willebrand factor
The promoter sequence has been described by Jahroudi and Lynch (Mol. Cell. Biol. 14, 999 (1994), Ferreira et al., Biochem. J. 293, 641 (1993) and Aird et al., PNAS USA 92, 4567 (1995)).

IL-1α and IL-1β
IL-1 is produced by activated endothelial cells (Warner et al., J. Immunol. 139, 1911 (1987)).
The promoter sequences have been described by Hangen et al., Mol. Carcinog. 2, 68 (1986), Turner et al., J. Immunol. 143, 3556 (1989), Fenton et al., J. Immunol. 138, 3972 (1987), Bensi et al., Cell Growth Diff. 1, 491 (1990), Hiscott et al., Mol. Cell. Biol. 13, 6231 (1993) and Mori et al., Blood 84, 1688 (1994).

IL-1 receptor The promoter sequence has been described by Ye et al., PNAS USA 90, 2295 (1993).

vascular cell adhesion molecule (VCAM-1) The expression of VCAM-1 in endothelial cells is activated by lipopolysaccharides, TNF-α (Neish et al., Mol. Cell. Biol. 15, 2558 (1995)), IL-4 (Iademarco et al., J. Clin. Invest. 95, 264 (1995)), IL-1 (Marni et al., J. Clin. Invest. 92, 1866 (1993)). The promoter sequence of VCAM-1 has been described by Neish et al., Mol. Cell. Biol. 15, 2558 (1995), Ahmad et al., J. Biol. Chem. 270, 8976 (1995), Neish et al., J. Exp. Med. 176, 1583 (1992), Iademarco et al., J. Biol. Chem. 267, 16323 (1992) and Cybulsky et al., PNAS USA 88, 7859 (1991).

Synthetic activator sequence As an alternative to natural endothelium-specific promoters, synthetic activator sequences can also be used which are composed of oligomerized binding sites for transcription factors which are preferentially or selectively active in endothelial cells. An example of such a transcription factor is the transcription factor GATA-2, whose binding site in the endothelin 1 gene is 5'-TTATCT-3' (Lee et at., Biol. Chem. 266, 16188 (1991), Dorfmann et al., J. Biol. Chem. 267, 1279 (1992) and Wilson et al., Mol. Cell. Biol. 10, 4854 (1990)).

b) Activator sequences which are activated in cells in the vicinity of activated endothelial cells In proliferating endothelia, neighboring cells become accessible to macromolecules of the blood through tight junctions which are opened. As a result of the functional and anatomical interrelationships, the neighboring cells of activated endothelial cells are target cells within the meaning of this invention.

VEGF
VEGF is formed by various cells (e.g. smooth muscle cells and tumor cells) in the immediate vicinity of proliferating endothelial cells, particularly under hypoxic conditions (Ferrara et al., Endoc. Rev. 13, 18 (1992), Berse et al., Mol. Biol. Cell 3, 211 (1992), Finkenzeller et al., BBRC 208, 432 (1995), Tischer et al., BBRC 165, 1198 (1989), Leung et al., Science 246, 1306 (1989)). The gene-regulatory sequences for the VEGF gene are
the promoter sequence of the VEGF gene (5'-flanking region) (Michenko et al., Cell Mol Biol. Res. 40, 35 (1994), Tischer et al., J. Biol. Chem. 266, 11947 (1991)) or the enhancer sequence of the VEGF gene (3'-flanking region) (Michenko et al., Cell Mol. Biol. Res. 40, 35 (1994) or the c-Src gene (Mukhopadhyay et al., Nature 375, 577 (1995), Bonham et al., Oncogene 8, 1973), Parker et al., Mol. Cell. Biol. 5, 831 (1985), Anderson et al., Mol. Cell. Biol. 5, 1122 (1985)) or the V-Src gene (Mukhodpadhyay et al., Nature 375, 577 (1995), Anderson et al., Mol. Cell. Biol. 5, 1122 (1985), Gibbs et al., J. Virol. 53, 19 (1985))

Steroid hormone receptors and their promoter elements (Truss and Beato, Endocr. Rev. 14, 459 (1993)), in particular the Mouse mammary tumor virus promoter In most cells, this promoter is activated by steroids, for example by glucocorticosteroids (Parks et al., Cell 8, 87 (1976)) or by progestins (Cato et al., EMBO J. 5, 2237 (1986)). The cDNA sequence of the promoter region of the long terminal repeat region of MMTV has been described by Chalepakis et al., Cell 53, 371 (1988) and Truss and Beato (Endocr. Rev. 14, 459 (1993).

2.2. Choice of the Repressor Module

As an example, a cell cycle-regulated promoter module is to be understood to be the nucleotide sequence CDE-CHR-lnr (see below). The essential function of this promoter module is to inhibit the function of the activator sequence in the G0/G1 phase of the cell cycle and to trigger cell cycle-specific expression in the S/G2 phase and consequently in proliferating cells.

Figure 2:
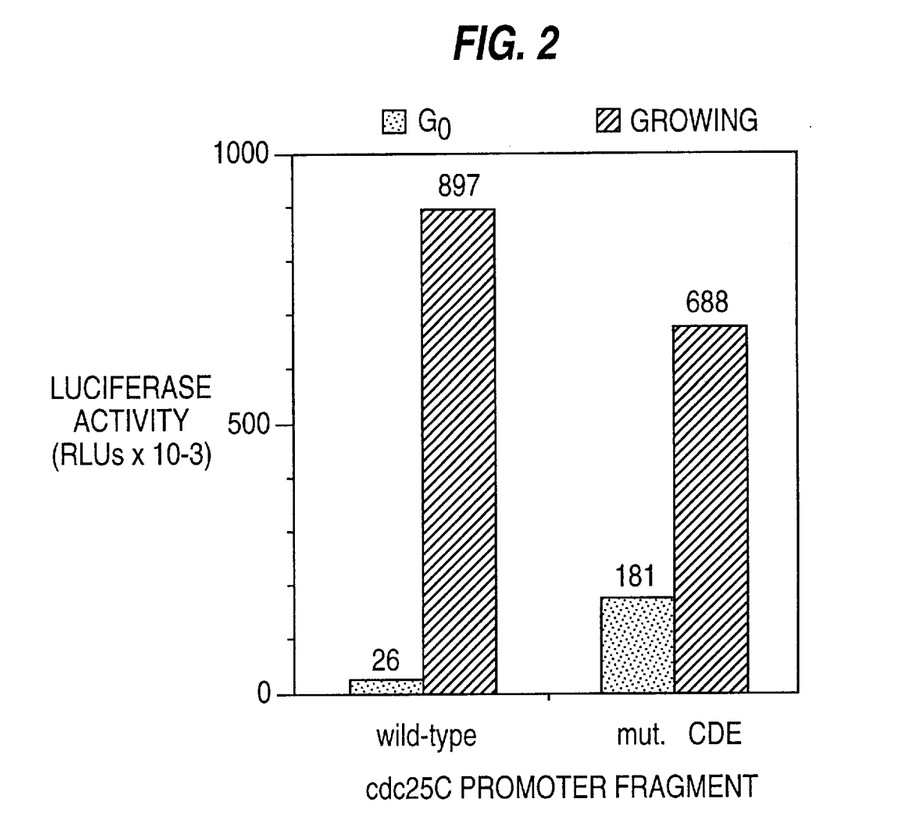
FIG. 2: Specific derepression of the cdc25C promoter in $G_0$ by mutating the cdc.
Figure 3:
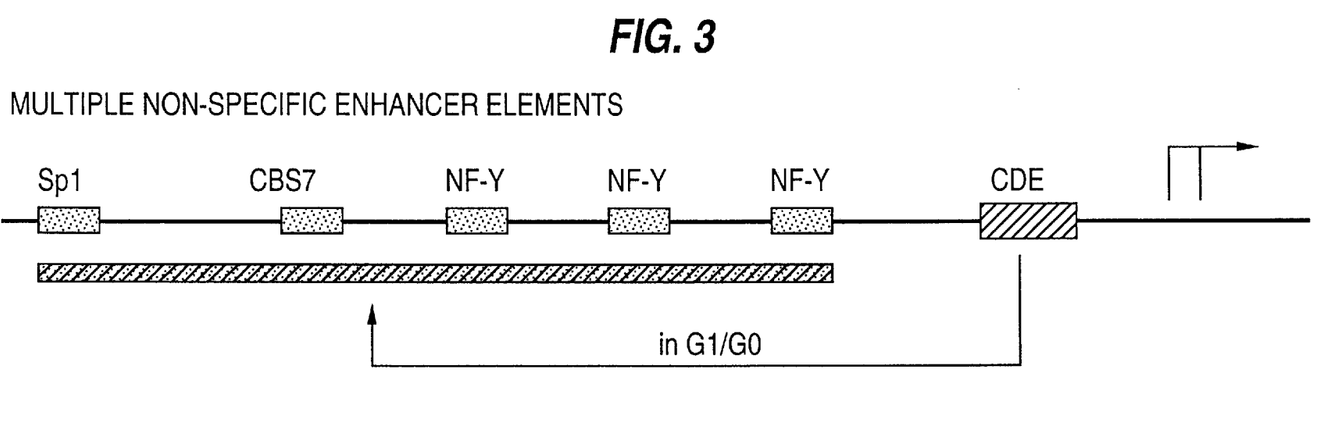
FIG. 3: Diagrammatic representation of the regulation of the cdc25C enhancer by the CDE.

The promoter module CDE-CHR-lnr was discovered in the context of a detailed investigation of the G2-specific expression of the human cdc25C promoter. The starting point was the discovery of a repressor element (cell cycle dependent element; CDE) which is responsible for switching off the promoter in the G1 phase of the cell cycle (Lucibello et al., EMBO J. 14, 132 (1995)). By means of genomic dimethyl sulfate (DMS) footprinting and functional analyses (FIGS. 1 and 2), it was possible to demonstrate that CDE binds a repressor (CDE-binding factor; CDF) in a G1-specific manner and thereby gives rise to inhibition of transcription in non-proliferating (G0) cells. In its repressing function, the CDE, which is located in the region of the basal promoter, is dependent on an upstream activating sequence (UAS). This led to the conclusion that the CDE-binding factor inhibits the transcription-activating effect of 5'-bound activator proteins in a cell cycle-dependent manner, i.e. in non-proliferating cells and in the G1 phase of the cell cycle (FIG. 3).

Figure 4:
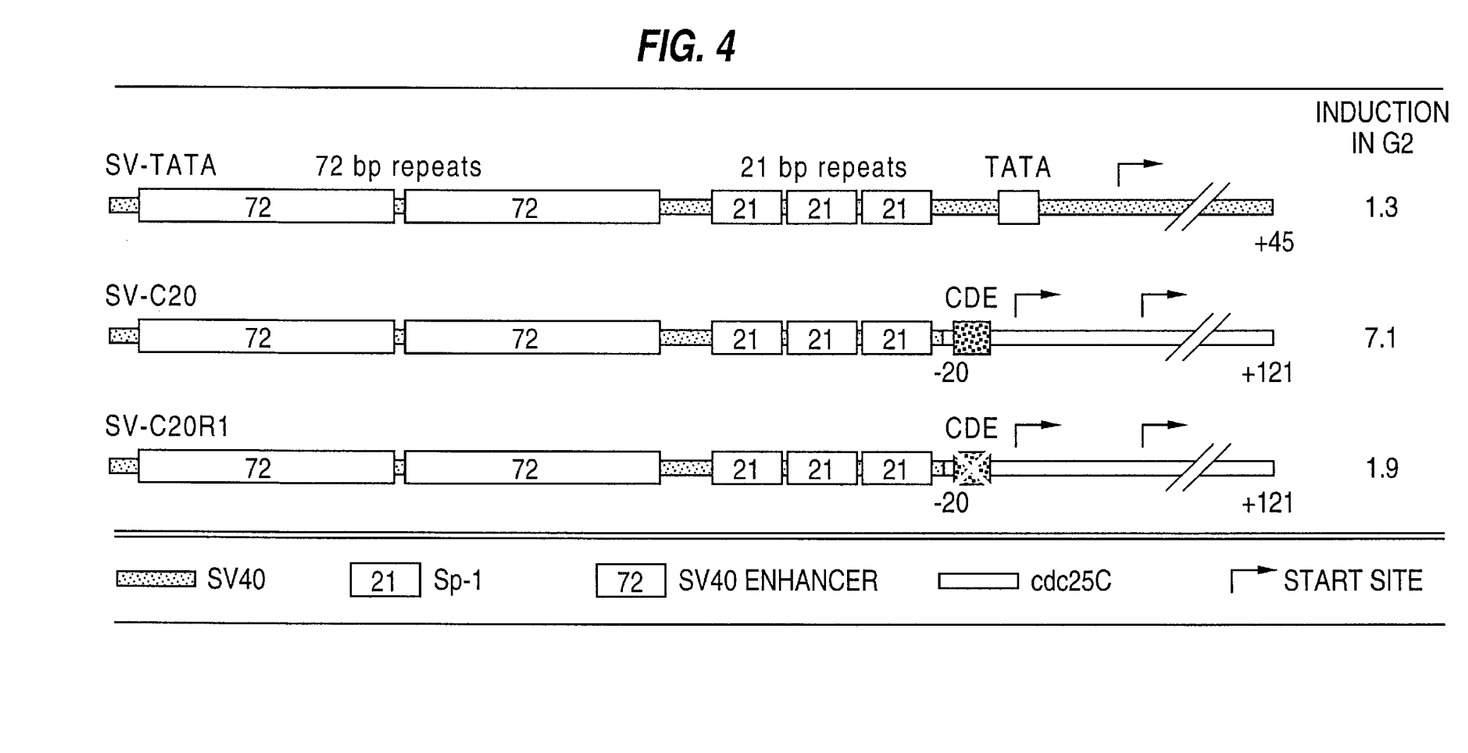
FIG. 4: $G_0/G_1$-specific repression of the SV40 enhancer by the CDE. The numbers on the right denote induction in G2 (in comparison to the control =1)

This conclusion was confirmed by a further experiment: Fusion of the viral, non-cell cycle-regulated early SV40 enhancer with a cdc25 minimal promoter (composed of CDE and the 3'-situated start sites) led to clear cell cycle regulation of the chimeric promoter (FIG. 4). Subsequent investigations of the cdc25C enhancer have shown that the transcription factors which are regulated by CDF in a cell cycle-dependent manner are NF-Y (synonym: CBF; Dorn et al., Cell 50, 863 (1987), van Hujisduijnen et al., EMBO J. 9, 3119 (1990), Coustry et al., J. Biol. Chem. 270, 468 (1995)), Sp1 (Kadonaga et al., TIBS 11, 10, 1986)) and a factor (CIF) which is possibly novel and which binds to CBS7. An additional interesting finding of this study was the observation that NF-Y within the cdc25C enhancer only activates transcription efficiently in cooperation with at least one further NF-Y complex or with CIF. Both NF-Y and Sp1 belong to the class of glutamine-rich activators, something which provides important information about the mechanism of repression (e.g. interaction or interference with particular basal transcription factors or TAFs).

Figure 5:
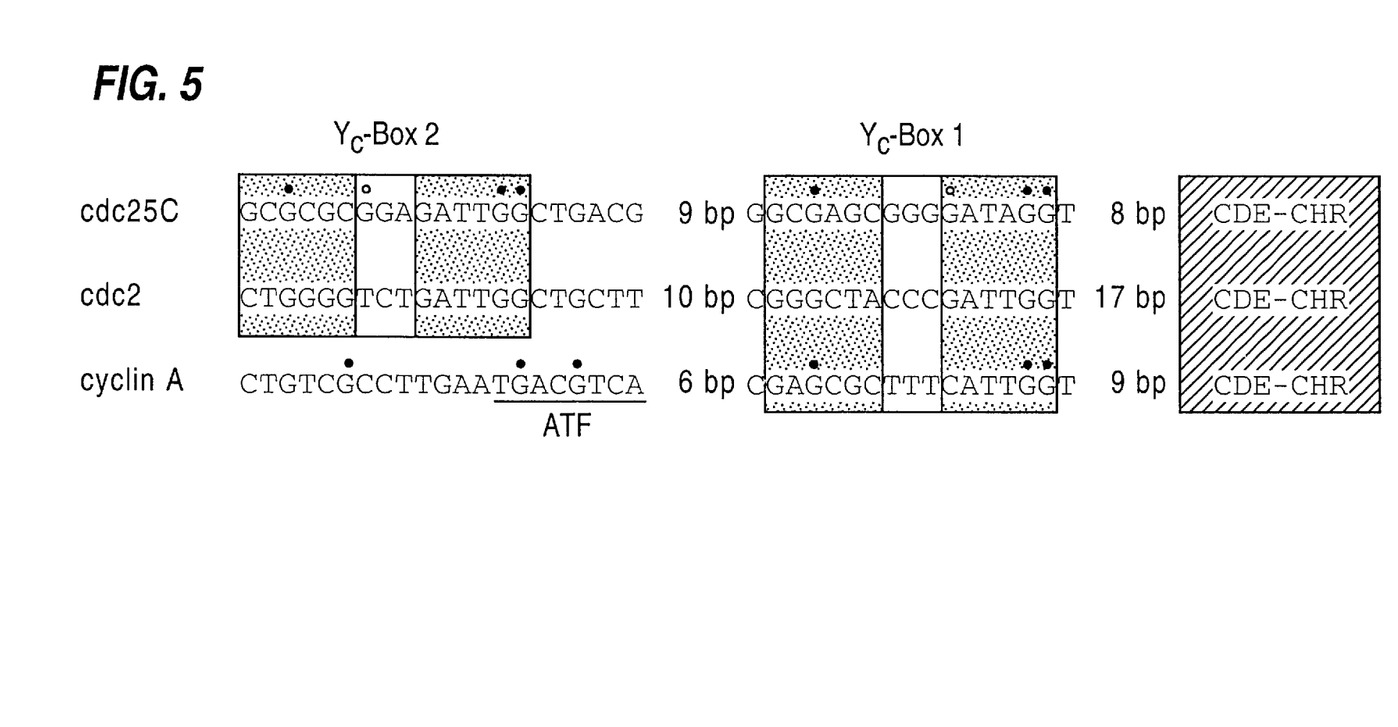
FIG. 5: Homologies in the CDE-CHR region and the 5'-situated Yc boxes, in the cdc25C, cyclin A and cdc2 promoters (SEQ ID NOS: 1–2, 5–6, and 3–4, respectively).

Comparison of the promoter sequences of cdc25C, cyclin A and cdc2 (SEQ ID NOS: 1–2, 5–6, and 3–4, respectively) demonstrated homologies in several regions (FIG. 5). Not only is the CDE conserved in all 3 promoters (the divergences which are present are not functionally relevant) but the neighboring $Y_c$ boxes are conserved as well. As expected, all these regions exhibited protein binding in vivo, with this protein binding being cell cycle-dependent in the case of the CDE. In addition, it was possible to demonstrate that all 3 promoters are deregulated by mutation of the CDE (Table 1). When the cdc25C, cyclin A and cdc2 sequences were compared, a remarkable similarity was also evident in the region immediately 3' of the CDE (cell cycle genes homology region; CHR) (FIG. 5). Although this region is functionally as important as the CDE (Table 1), it is not visible in the in-vivo DMS footprinting experiments. A possible explanation for this is an interaction of the factor with the minor groove of the DNA. Results from electrophoretic mobility shift assay (EMSA) experiments point to CDE and CHR together binding a protein complex, the CDF. These observations indicate that CDF-mediated repression of glutamine-rich activators is a frequently occurring mechanism of cell cycle-regulated transcription.

Figure 1:
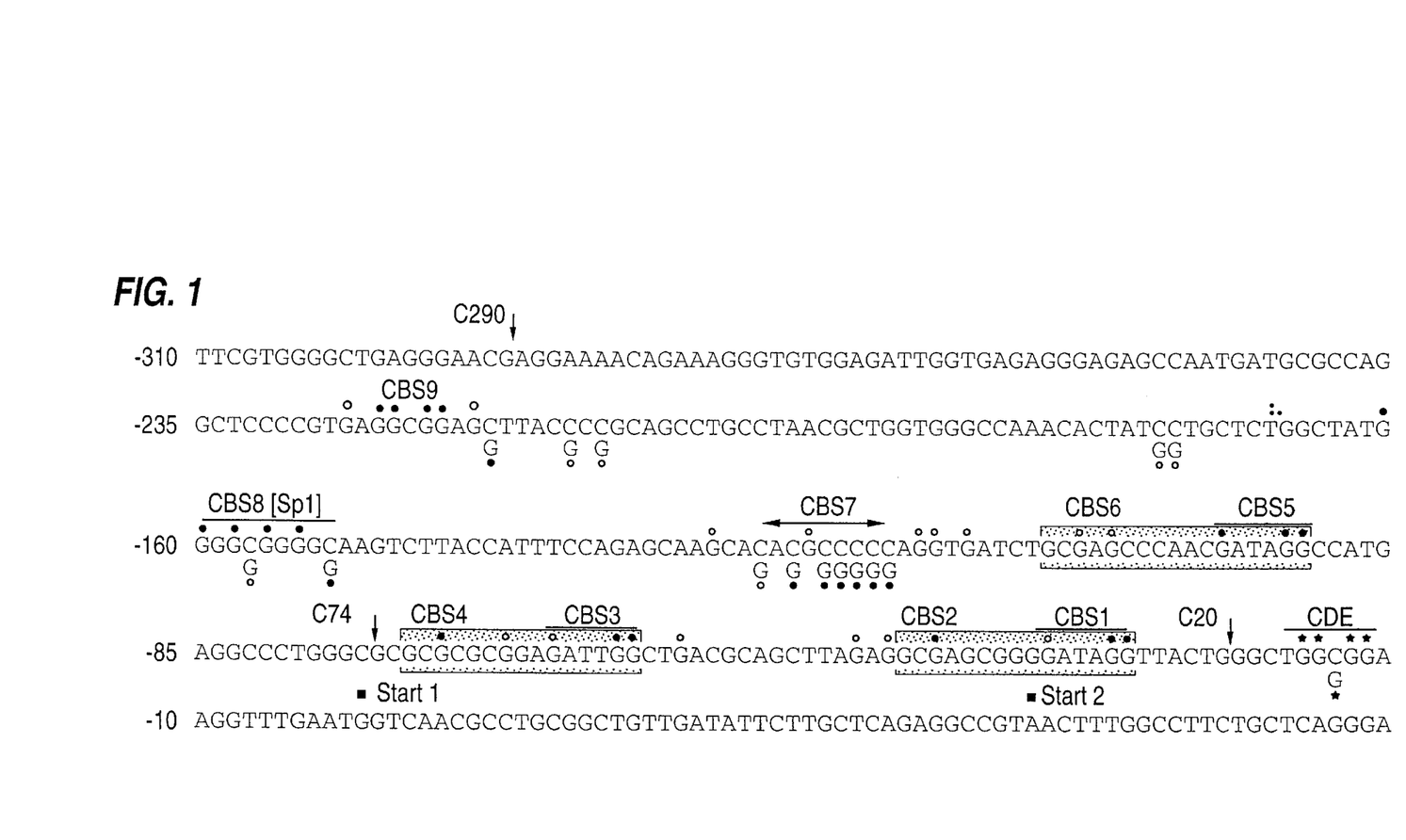
FIG. 1: Nucleotide sequence of the cdc25C promoter region together with the protein binding sites which have been found in vivo (genomic DMS footprinting; • (filled circles): complete constitutive protection; ○ (open circles): partial constitutive protection; * (asterisk): cell cycle-regulated, G1-specific protection). CBS: constitutive binding site; CDE: cell cycle-dependent element. Regions underlaid in gray indicate the $Y_c$ boxes (NF-Y binding sites). Start sites are marked by filled squares (SEQ ID NO: 7 is shown in this Figure).

However, it is apparently not only the CDE-CHR region which is of importance for regulating the cdc25C promoter but also one of the initiation sites (position +1) within the nucleotide sequence of the basal promoter (positions $\leq-20$ to $\geq+30$, see FIG. 1). Mutations in this region, which encompasses the in-vitro binding site for YY-1 (Seto and Shenk, Nature 354, 241 (1991), Usheva and Shenk, Cell 76, 1115 (1994)) lead to complete deregulation. In view of the proximity of the CDE-CHR to the basal promoter, interaction of the CDF with the basal transcription complex is consequently very probable.

2.3. Choice of the Antitumoral Substance a) Inhibitors of proliferation

Within the meaning of this invention, an antitumoral substance is to be understood as being the DNA sequence of a protein which inhibits the proliferation of endothelial cells. Examples of these DNA sequences are the DNA sequences, which are listed in the following literature references, for retinoblastoma protein (pRb/p110) or for its analogs p107 and p120 (La Thangue, Curr. Opin. Cell Biol. 6, 443 (1994))

protein p53 (Prives et al., Genes Dev. 7, 529 (1993))

protein p21 (WAF-1) (El-Deiry et al., Cell 75, 817 (1993))

protein p16 (Serrano et al., Nature 366, 704 (1993), Kamb et al., Science 264, 436 (1994), Nobori et al., Nature 368, 753 (1994))

other CdK inhibitors (review in Pines, TIBS 19, 143 (1995))

GADD45 protein (Papathanasiou et al., Mol. Cell. Biol. 11, 1009 (1991), Smith et al., Science 266, 1376 (1994))

bak protein (Farrow et al., Nature 374, 731 (1995) Chittenden et al., Nature 374, 733 (1995), Kiefer et al., Nature 374, 736 (1995))

In order to prevent rapid intracellular inactivation of these cell cycle inhibitors, those genes should preferably be used which possess mutations for the inactivation sites of the expressed proteins without the function of these proteins thereby being impaired.

Retinoblastoma protein (pRb) and the related p107 and p130 proteins are inactivated by phosphorylation. Consequently, a pRb/p110, p107 or p130 cDNA sequence is used which is point-mutated such that the phosphorylation sites of the encoded protein are replaced with amino acids which cannot be phosphorylated.

According to Hamel et al. (Mol. Cell. Biol. 12, 3431 (1992)), retinoblastoma protein (pRb/p110) can no longer be phosphorylated when the amino acids in positions 246, 350, 601, 605, 780, 786, 787, 800 and 804 have been replaced; nevertheless, these replacements do not impair its activity in binding to the large T antigen. For example, in the pRb/p110 protein, the amino acids Thr-256, Ser-601, Ser-605, Ser-780, Ser-786, Ser-787 and Ser-800 are replaced with Ala, the amino acid Thr-350 is replaced with Arg and the amino acid Ser-804 is replaced with Glu.

The DNA sequence for the p107 protein or the p130 protein is mutated in an analogous manner.

Protein p53 is inactivated in the cell either by binding to special proteins, such as MDM2, or by oligomerization of the p53 by way of the dephosphorylated C-terminal serine 392 (Schikawa et al., Leukemia and Lymphoma 11, 21 (1993) and Brown, Annals of Oncology 4, 623 (1993)). Consequently, a p53 cDNA sequence is preferably used which is truncated C-terminally by removing the serine 392.

b) Angiogenesis inhibitors

An antitumoral substance is furthermore to be understood to be the DNA sequence for a protein which inhibits angiogenesis. Particular examples of these proteins (the relevant DNA sequence is referred to in the cited literature) are:

plasminogen activator inhibitor 1 (PAI-1) (Reilly et al., J. Biol. Chem. 265, 9570 (1990), Bosma et al., J. Biol. Chem. 253, 9219 (1988))

PAI-2 (Steven et al., Eur. J. Biochem. 196, 431 (1991))

PAI-3 (Meijers et al., J. Biol. Chem. 266, 15028 (1991))

angiostatin (O'Reilly et al., Cell 79, 315 (1994), Bicknell et al., Semin. Cancer Biol. 3, 399 (1992))

interferons (Dorr, Drugs 45, 177 (1993), Drugs of Today 22, 597 (1986), US 45 185 84, US 45 88 585), specifically IFNα (Henco et al., J. Mol. Biol. 185, 227 (1985), Pestka et al., Ann. Rev. Biochem. 56, 727 (1987), Weissmann et al., Phil. Trans. R. Soc. Lond. B299, 7 (1982), Goeddel et al., Nature 290, 20 (1981))

IFNβ (Sen et al., J. Biol. Chem. 267, 5017 (1992), Mark et al., EP 192 811, EP 234 599, US 45 88 585)

IFNγ (Gray et al., Nature 295, 503 (1982), Yip et al., PNAS USA 79, 1820 (1982), Rinderknecht et al., J. Biol. Chem. 259, 6790 (1984))

platelet factor 4 (Mc Manus et al., J. Immunol. 123, 2835 (1979); Brindley et al., J. Clin. Invest. 72, 1218 (1983); Deuel et al., Proc. Natl. Acad. Sci. USA 78, 4584, 1981))

IL-12 (Voest et al., N. Natl. Cancer Inst. 87, 581 (1995), Wolf et al., J. Immunol. 146, 3074 (1991), Gubler et al., PNAS USA 88, 4143 (1991), Kobayashi et al., J. Exp. Med. 170, 827 (1989), Gabler et al., PNAS 88, 4143 (1991), Gately et al., J. Immunol. 147, 874 (1991), Schoenhaut et al., J. Immunol. 148, 3433 (1992), Wolf et al., J. Immunol. 146, 3074 (1991))

TIMP-1 (Kolkenbrock et al., Eur. J. Biochem. 198, 775 (1991), Faucher et al., Path. Biol. 37, 199 (1989))

TIMP-2 (Kolkenbrock et al., Eur. J. Biochem. 198, 775 (1991))

TIMP-3 (Wick et al., J. Biol Chem. 269, 18953 (1994)).

leukemia inhibitory factor (LIF) (Pepper et al., J. Cell Science 108, 73 (1995), Gough et al., Ciba Found. Symp. 167, 24 (1992), PNAS USA 85, 5971 (1988), Stahl et al., J. Biol. Chem. 265, 8833 (1990), Rathjan et al., Cell 62, 1105 (1990))

c) Cytostatic and cytotoxic proteins

However, an antitumoral substance is also to be understood to be a DNA sequence for a protein which directly or indirectly exhibit a cytostatic effect on tumors. These proteins include, in particular perforin (Lin et al., Immunol. Today 16, 194 (1995))

granzyme (Smyth et al., Immunol. Today 16, 202 (1995))

IL-2 (Fietscher et al., Lymphok. Res. 6, 45 (1987), Matsui et al., Lymphokines 12, 1 (1985), Tanaguchi et al., Nature 302, 305 (1983))

IL-4 (Lee et al., PNAS 83, 2061 (1986); Paul, Blood 77, 1859 (1991), Yokota et al., PNAS USA 83, 5894 (1986), van Leuven et al., Blood 73, 1142 (1989), Arai et al., J. Immunol. 42, 274 (1989)

IL-12 (Kobayashi et al., J. Exp. Med. 170, 827 (1989), Gabler et al., PNAS 88, 4143 (1991), Gately et al., J. Immunol. 147, 874 (1991), Schoenhaut et al., J. Immunol. 148, 3433 (1992), Wolf et al., J. Immunol. 146, 3074 (1991))

interferons, such as

IFN-α (Henco et al., J. Mol. Biol. 185, 227 (1985), Pestka et al., Ann. Rev. Biochem. 56, 727 (1987), Weissmann et al., Phil. Trans. R. Soc. Lond. B299, 7 (1982), Goeddel et al., Nature 290, 20 (1981))

IFNβ (Sen et al., J. Biol. Chem. 267, 5017 (1992), Mark et al., EP 192 811, EP 234 599, US 45 88 585)

IFNγ (Gray et al., Nature 295, 503 (1982), Yip et al., PNAS USA 79, 1820 (1982), Rinderknecht et al., J. Biol. Chem. 259, 6790 (1984))

TNF (Porter, TiBTech 9, 158 (1991); Sidhu et al., Pharmac. Ther. 57, 79 (1993)), especially TNFα (Beutler et al., Nature 320, 584 (1986). Kriegler et al., Cell 53, 45 (1988))

TNFβ (Gray et al., Nature 312, 721 (1984), Li et al., J. Immunol. 138, 4496 (1987), Aggarwal et al., J. Biol. Chem. 260, 2334 (1985))

oncostatin M (Brown et al., J. Immunol. 147, 2175 (1991); Grove et al., J. Biol. Chem. 266, 18194 (1991); Hamilton et al., Biochem. Biophys. Res. Commun. 180, 652 (1991), Malik et al., Mol. Cell. Biol. 9, 2847 (1989), Kallstad et al., J. Biol. Chem. 266, 8940 (1991))

d) Inflammation inducers

An antitumoral substance is furthermore to be understood to be the DNA sequence for a protein which, where appropriate in addition to the antitumoral effect, stimulate inflammations and thereby contributes to eliminating tumor cells. Particular examples of these proteins are:

RANTES (MCP-2) (Schall et al., J. Immunol. 141, 1018 (1988), Cell 61, 361 (1990))

monocyte chemotactic and activating factor (MCAF) (Zachariae et al., J. Exp. Med. 171, 2177 (1990); Rollins et al., Blood 78, 1112 (1991); Mukaida et al., J. Immunol. 146, 1212 (1991); Sica et al., J. Immunol. 144, 3034 (1990))

IL-8 (Lotz et al., J. Immunol. 148, 466 (1992); Clore et al., Biochemistry 29, 1689 (1990), Matsushima et al., J. Exp. Med. 167, 1883 (1988), Baglioni et al., J. Clin. Invest. 84, 1045 (1989), Int. J. Immunopharm. 17, 103 (1995), Carre et al., J.Clin. Invest. 88, 1802 (1991))

macrophage inflammatory protein 1 (MIP-1 α and MIP-1β) (Broxmeyer et al., J. Immunol. 147, 2586 (1991); Oh et al., J. Immunol. 147, 2978 (1991); Graham et al., Nature 344, 442 (1990))

neutrophil activating protein 2 (NAP-2) (Walz, Rheum. Arthr., London (1991), Chang et al., J. Biol. Chem. 269, 25277 (1994))

IL-3 (Otsuka et al., J. Immunol. 140, 2288 (1988); de Vries et al., Stem Cells 11, 72 (1993), Yang et al., Blood 71, 958 (1988), Cell 47, 3 (1986), Philips et al., Gene 84, 501 (1989))

IL-5 (Azuma et al., Nucl. Acid Res. 14, 9149 (1986); Yokota et al., PNAS 84, 7388 (1987); Campbell et al., PNAS 84, 6629 (1987), Azuma et al., Nucl. Acids Res. 14, 9149 (1986))

human leukemia inhibitory factor (LIF) (Gough et al., Ciba Found. Symp. 167, 24 (1992), PNAS USA 85, 5971 (1988), Stahl et al., J. Biol. Chem. 265, 8833 (1990), Rahtjan et al., Cell 62, 1105 (1990))

IL-7 (Matzuda et al., Leuk. Lymph. 5, 231 (1991), Lupton et al., J. Immunol. 144, 3592 (1990), Goodwin et al., PNAS USA 86, 302 (1989), Swatherland et al., Hum. Genet. 82, 371 (1989))

IL-11 (Paul et al., Proc. Natl. Acad. Sci. USA 87, 7512 (1990), Teramura et al., Blood 79, 327 (1992), Kawashima et al., FEBS Lett. 283, 199 (1991))

IL-13 (McKenzie et al., J. Immunol. 150, 5436 (1993), Muzio et al., Blood 83, 1738 (1994), McKenzie et al., PNAS 90, 3735 (1993), Minty et al., Nature 362, 248 (1993))

GM-CSF (Wong et al., Science 228, 810 (1985), Gough et al., Nature 309, 763 (1984), Nicola et al., J. Biol. Chem. 254, 5290 (1979))

G-CSF (Nagata et al., EMBO J. 5, 575 (1986), Nagata et al., Nature 319 415 (1986), Souza et al., Science 232 61(1986))

M-CSF (Welte et al., PNAS 82, 1526 (1985), Lu et al., Arch. Biochem. Biophys. 268, 81 (1989), Kawasaki et al., Science 230, 291 (1985), Suzu et al., J. Biol. Chem. 267, 4345 (1992), Wong et al., Science 235, 1504 (1987))

DNA sequences of fusion proteins which are formed between the listed cytokines, on the one hand, and the Fc moiety of human immunoglobulin, on the other hand, may also be used as active substances within the meaning of the invention. DNA sequences of this nature, and their preparation, have been described in EPA 0464 633 A1.

e) Enzymes for activating precursors of cytostatic agents

However, an antitumoral substance is also to be understood as being the DNA sequence of an enzyme which is able to convert precursors of an antitumoral active compound into an antitumoral active compound. Enzymes of this nature, which cleave inactive precursor substances (prodrugs) and thereby form active cytostatic agents (drugs), and the prodrugs and drugs which are in each case pertinent, have already been reviewed by Deonarain et al. (Br. J. Cancer 70, 786 (1994), by Mullen, Pharmac. Ther. 63, 199 (1994) and by Harris et al., Gene Ther. 1, 170 (1994)).

For example, use is to be made of the DNA sequence for one of the following enzymes:

herpes simplex virus thymidine kinase (Garapin et al., PNAS USA 76, 3755 (1979), Vile et al., Cancer Res. 53, 3860 (1993), Wagner et al., PNAS USA 78, 1441 (1981), Moelten et al., Cancer Res. 46, 5276 (1986), J. Natl. Cancer Inst. 82, 297 (1990))

varicella zoster virus thymidine kinase (Huber et al., PNAS USA 88, 8039 (1991), Snoeck, Int. J. Antimicrob. Agents 4, 211 (1994))

bacterial nitroreductase (Michael et al., FEMS Microbiol. Letters 124, 195 (1994), Bryant et al., J. Biol. Chem. 266, 4126 (1991), Watanabe et al., Nucleic Acids Res. 18, 1059 (1990))

bacterial β-glucuronidase (Jefferson et al., PNAS USA 83, 8447 (1986)

plant β-glucuroniase from Secale cereale (Schulz et al., Phytochemistry 26, 933 (1987))

human β-glucuronidase (Bosslet et al., Br. J. Cancer 65, 234 (1992), Oshima et al., PNAS USA 84, 685 (1987))

human carboxypeptidase (CB), e.g.
mast cell CB-A (Reynolds et al., J. Clin. Invest. 89, 273 (1992))
pancreatic CB-B (Yamamoto et al., J. Biol. Chem. 267, 2575 (1992), Catasus et al., J. Biol. Chem. 270, 6651 (1995))
bacterial carboxypeptidase (Hamilton et al., J. Bacteriol. 174, 1626 (1992), Osterman et al., J. Protein Chem. 11, 561 (1992))

bacterial β-lactamase (Rodrigues et al., Cancer Res. 55, 63 (1995), Hussain et al., J. Bacteriol. 164, 223 (1985), Coque et al., Embo J. 12, 631 (1993)

bacterial cytosine deaminase (Mullen et al., PNAS USA 89, 33 (1992), Austin et al., Mol. Pharmac. 43, 380 (1993), Danielson et al., Mol. Microbiol. 6, 1335 (1992)

human catalase or peroxidase (Ezurum et al., Nucl. Acids Res. 21, 1607 (1993))

phosphatase, in particular
human alkaline phosphatase (Gum et al., Cancer Res. 50, 1085 (1990))
human acid prostate phosphatase (Sharieff et al., Am. J. Hum. Gen. 49, 412 (1991), Song et al., Gene 129, 291 (1993), Tailor et al., Nucl. Acids Res. 18, 4928 (1990))
type 5 acid phosphatase (Gene 130, 201 (1993))

oxidase, in particular
human lysyl oxidase (Kimi et al., J. Biol. Chem. 270, 7176 (1995))
human acid D-amino oxidase (Fukui et al., J. Biol. Chem. 267, 18631 (1992))

peroxidase, in particular
human gluthatione peroxidase (Chada et al., Genomics 6, 268 (1990), Ishida et al., Nucl. Acids Res. 15, 10051 (1987))
human eosinophilic peroxidase (Ten et al., J. Exp. Med. 169, 1757 (1989), Sahamaki et al., J. Biol. Chem. 264, 16828 (1989))
human thyroid peroxidase (Kimura, PNAS USA 84, 5555 (1987)).

In order to facilitate secretion of the listed enzymes, the homologous signal sequence which is in each case containing in the DNA sequence can be replaced by a heterologous signal sequence which improves extracellular secretion.

Thus, for example, the signal sequence of β-glucuronidase (DNA position ≦27 to 93; Oshima et al., PNAS 84, 685 (1987)) can be replaced by the signal sequence for immunoglobulin (DNA position ≦63 to ≧107; Riechmann et al., Nature 332, 323 (1988)).

In addition, DNAs are preferably to be chosen of those enzymes which, as a result of point mutations, are stored to a lesser extent in lysosomes and are secreted to an increased extent. Point mutations of this nature have been described, for example, for β-glucuronidase (Shiplex et al., J. Biol. Chem. 268, 12193 (1993)).

2.4. Combination of Several Antitumoral Substances

The invention furthermore relates to an active compound in which the DNA sequences of several identical antitumoral substances (A,A) or of different antitumoral substances (A,B) are combined. For the expression of two DNA sequences, the cDNA of an internal ribosome entry site (IRES) is preferably interposed as a regulatory element.

Such IRESs have been described, for example, by Mountford and Smith (TIG 11, 179 (1995), Kaufman et al., Nucl. Acids Res. 19, 4485 (1991), Morgan et al., Nucl. Acids Res. 20, 1293 (1992, Dirks et al., Gene 128, 247 (1993), Pelletier and Sonenberg, Nature 334, 320 (1988) and Sugitomo et al., BioTechn. 12, 694 (1994).

Thus, the cDNA of the IRES sequence of poliovirus (position ≦140 to ≧630 of the 5' UTR; Pelletier and Sonenberg, Nature 334, 320 (1988)) can be used to link the DNA of anti-inflammatory substance A (at the 3' end) and the DNA of anti-inflammatory substance B (at the 5' terminus).

Depending on the combination (A+A, A+B1) an active compound of this nature exhibits either an additive or a synergistic effect within the meaning of the invention.

2.5. Construction of the Vector

The novel DNA construct is made into a complete vector in a manner with which the skilled person is familiar. This vector can be of viral or non-viral origin. For example, the novel DNA construct is inserted into a viral vector (in this regard, see D. Jolly, Cancer Gene Therapy 1, 51 (1994)) or else is used as a plasmid. Viral vectors or plasmids can be complexed with colloidal dispersions, for example with liposomes (Farhood et al., Annals of the New York Academy of Sciences 716, 23 (1994)), or else formulated as pharmaceuticals together with a polylysine/ligand conjugate (Curiel et al., Annals of the New York Academy of Sciences 716, 36 (1994)) or other customary auxiliary substances.

2.6. Choice of the Ligand

Viral and non-viral vectors can be supplemented with a ligand. Substances which bind to the surface of proliferating endothelial cells are preferred as ligands, for example in polylysine/ligand conjugates. These substances include antibodies or antibody fragments which are directed against membrane structures of endothelial cells, as have been described, for example, by Burrows et al. (Pharmac. Ther. 64, 155 (1994)), Hughes et al. (Cancer Res. 49, 6214 (1989) and Maruyama et al. (PNAS-USA 87, 5744 (1990). These substances in particular include antibodies against VEGF receptors.

The murine monoclonal antibodies are preferably to be employed in humanized form. They are humanized in the manner described by Winter et al. (Nature 349, 293 (1991) and Hoogenbooms et al. (Rev. Tr. Transfus. Hemobiol. 36, 19 (1993)). Antibody fragments are prepared in accordance with the state of the art, for example in the manner described by Winter et al., Nature 349, 293 (1991), Hoogenboom et al., Rev. Tr. Transfus. Hemobiol. 36, 19 (1993), Girol, Mol. Immunol. 28, 1379 (1991) or Huston et al., Intern. Rev. Immunol. 10, 195 (1993).

The ligands furthermore include all active compounds which bind to membrane structures or membrane receptors on endothelial cells. For example, they include substances which contain mannose terminally and, in addition, IL-1 or growth factors, or their fragments or constituent sequences thereof, which bind to receptors which are expressed by endothelial cells, for example PDGF, bFGF, VEGF, and TGFβ (Pusztain et al., J. Pathol. 169, 191 (1993)). In addition, they include adhesion molecules which bind to activated and/or proliferating endothelial cells. Adhesion molecules of this nature, for example SLex, LFA-1, MAC-1, LECAM-1 or VLA4, have already been described (reviews in Augustin-Voss et al., J. Cell Biol. 119, 483 (1992), Pauli et al., Cancer Metast. Rev. 9, 175 (1990) and Honn et al., Cancer Metast. Rev. 11, 353 (1992)).

2.7 Preparation of the Active Compound (Examples)

The preparation of the novel active compound is described in more detail with the aid of the following examples:

a) Construction of the chimeric promoter endothelin 1-CDE-CHR-lnr

Figure 6:
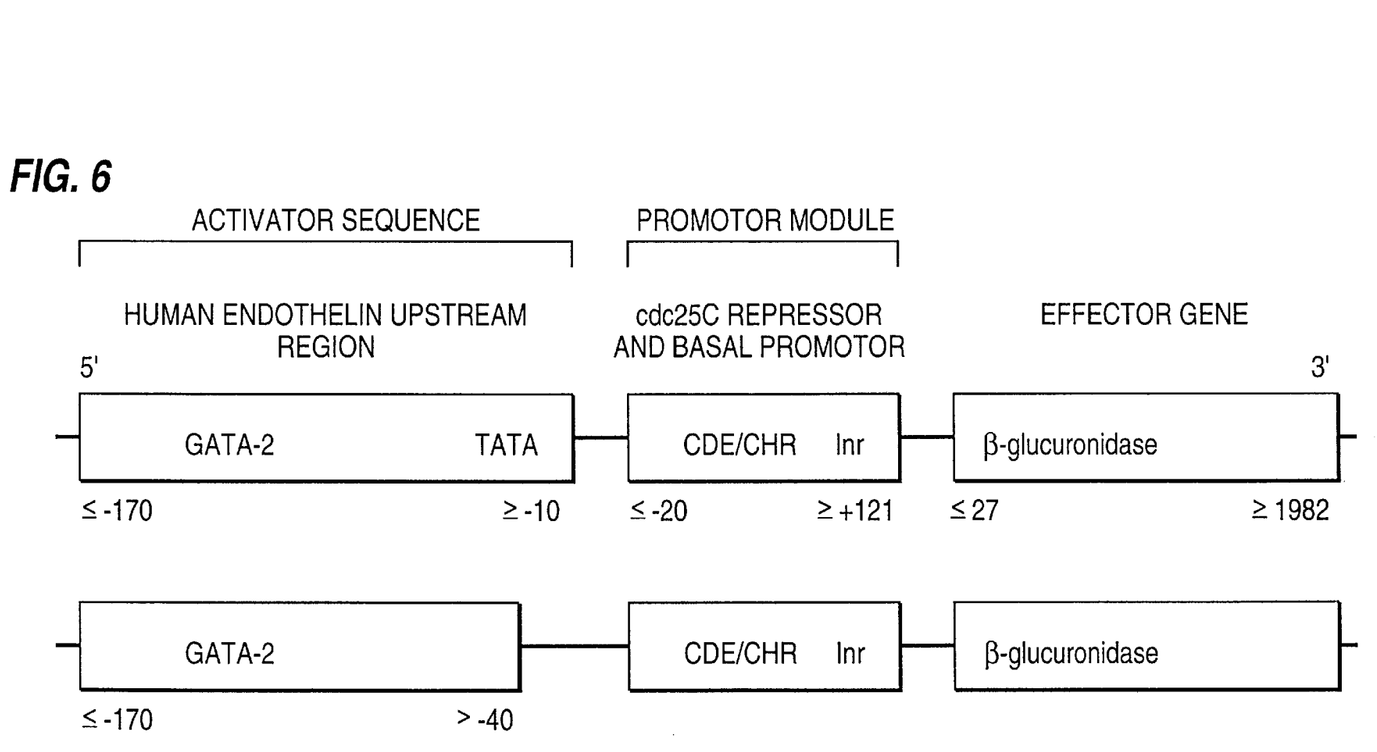
FIG. 6: Chimeric constructs which are composed of different moieties of the human endothelin-1 promoter, the 3'-fused promoter module containing the CDE and CHR repressor elements and a DNA for human β-glucuronidase (complete coding region, position $\leq 239$ – $\geq 2194$; Oshima et al., PNAS USA 84, 685 (1987) as effector. Position designations refer to the designations of Wilson et al., Mol. Cell. Biol. 10, 4854 (1990) for the endothelin 1 gene and to the system for cdc25C used by Lucibello et al., EMBO J. 15, 132 (1995), respectively.
Figure 7A:
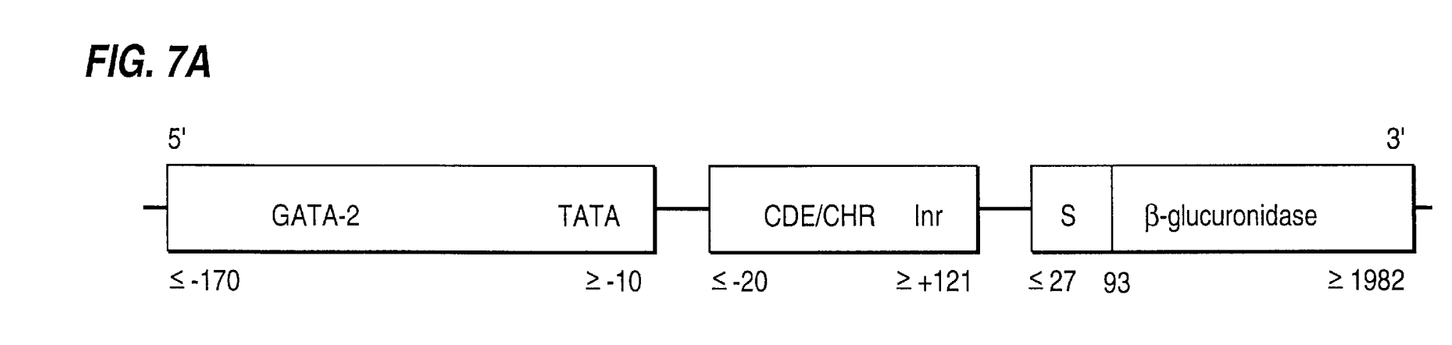
FIGS. 7A–7B: Position designation for the signal sequence (MGWSCIILFLVATAT, SEQ ID NO: 8) of the immunoglobulin (HuVHCAMP) refer to Riechmann et al., Nature 332, (1988)
Figure 7B:
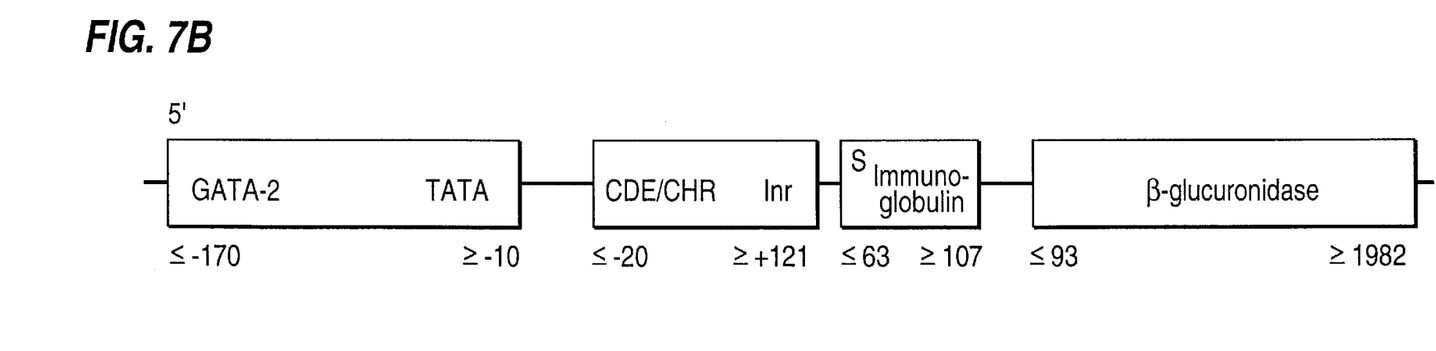

The human endothelin-1 promoter (position ≦−170 to ≧−10), or a variant which has been truncated by removing the TATA box (position ≦−170 to ≧−40), are linked, at its 3' end, to the 5' terminus of the CDE-CHR-lnr module (position ≦−20 to ≧+121) of the human cdc25C gene (FIG. 6). The linkage is effected using enzymes which are known to the skilled person and which are commercially available.

b) Construction of a plasmid which contains the central component of the active compound The chimeric endothelin-1 promoter module/transcription unit which has been described is linked, at their 3' ends, to the 5' terminus of a DNA which [lacuna] the complete coding region of human β-glucuronidase (position ≦27 to ≧1982; Oshima et al., PNAS USA 84, 685 (1987)). This DNA also contains the signal sequence (22 N-terminal amino acids) which is required for secretion. In order to facilitate the secretion from the cell, this signal sequence is preferably to be replaced with the immunoglobulin signal sequence (position ≦63 to ≧107; Riechmann et al., Nature 332, 323 (1988), see FIG. 7). Transcription control units and the DNA for P-glucuronidase are cloned into pUC19/19 or Bluescript-derived plasmid vectors, which can be employed directly, or in colloidal dispersion systems, for in-vivo administration. Alternatively, the chimeric genes can be transferred into viral vectors, or other suitable vectors, and injected.

2.8 Activity of the Active Compound

Following local administration, for example at the site of the tumor, or following intracranial or subarachnoid administration, or systemic, preferably intravenous or intraarterial administration, an active compound according to the present invention enables, by means of the combination of tissue-specific activator sequence (UAS) and cell cycle-regulated repressor module, endothelial cells, which are mainly, if not exclusively, only proliferating endothelial cells, or neighboring cells of these proliferating endothelial cells, to secrete substances which either inhibit proliferation themselves or else induce the-formation of substances which have an antiproliferative or cytostatic effect. The inhibition of endothelial cell proliferation, and/or the liberation of cytostatic substances, result(s) in inhibition of the growth of the tumor. The active compound is well tolerated since the formation of the antitumoral substance is restricted by the novel active compound to the site of tumor growth and the angiogenesis which is caused by the tumor.

Since the active compound promises a high degree of safety, both because of its cell specifity and its cell cycle specifity, it can also be used at high doses and, if necessary, repeatedly at intervals of days or weeks, for the therapy of tumor diseases.

LEGENDS TO FIGS. 1–7:

Alternative: Insertion of the Ig signal peptide in order to obtain improved extracellular secretion of the β-glucuronidase (FIG. 7B)

TABLE 1

Role of CDE and CHR in the cell cycle-regulated transcription of cdc25C, cyclin A and cdc2

Tab. 1

|  | $G_0$ | Growing | Factor |
|---|---|---|---|
| wt |  |  |  |
| cdc25C | 0.8 | 13.1 | 17.5 |
| cyclin A | 0.7 | 27.1 | 41.7 |
| cdc2 | 1.0 | 41.2 | 41.2 |
| mCDE(−13) |  |  |  |
| cdc25C | 7.6 | 11.6 | 1.5 |
| cyclin A | 13.4 | 23.9 | 1.8 |
| cdc2 | 11.3 | 33.9 | 3.0 |
| mCHR(−6/−3) |  |  |  |
| cdc25C | 14.4 | 21.0 | 1.5 |
| cyclin A | 15.5 | 28.3 | 1.8 |
| cdc2 | 18.6 | 38.6 | 2.1 |

The results of transient transfections in HIH3T3 cells are depicted as RLUs/1000. mCDE: mutated CDE (Pos. −13:G→T); mCHR: mutated CHR (Pos. −6 to −3).

What is claimed is:

1. A DNA construct for the prophylaxis or therapy of tumor diseases, which comprises an activator sequence, a cell cycle-regulated promoter module, and a DNA sequence encoding an antitumor substance, wherein said promoter module comprises a cell cycle dependent element, a cell cycle homology region, and an initiation site.

2. A DNA construct as claimed in claim 1, wherein said promoter module comprises the DNA sequence of base 291 through base 340 of SEQ ID NO:7.

3. A DNA construct as claimed in claim 1, wherein said cell cycle dependent element has the nucleotide sequence TGGCGG.

4. A DNA construct as claimed in claim 1, wherein said cell cycle gene homology region has the nucleotide sequence GTTTGAA.

5. A DNA construct as claimed in claim 1, wherein said activator sequence is regulated by transcription factors which are formed in endothelial cells or in cells which are in the immediate vicinity of proliferating endothelial cells.

6. A DNA construct as claimed in claim 1, wherein said activator sequence is selected from the group consisting of: the CMV promoter, the CMV enhancer and the SV40 promoter.

7. A DNA construct as claimed in claim 1, wherein said activator sequence is a promoter for a gene encoding a protein selected from the group consisting of endothelial glucose-1 transporter, endoglin, VEGF receptor 1, VEGF receptor 2, receptor tyrosine kinase til-1, receptor tyrosine kinase til-2, B61 receptor, B61 ligand, endothelin, endothelin B, endothelin 1, mannose 6-phosphate receptor, IL-1α, IL-1β, IL-1 receptor, VCAM-1, and von Willebrand factor.

8. A DNA construct as claimed in claim 1, wherein said activator sequence is an oligomerized binding site for a transcription factor which is preferentially active in endothelial cells.

9. A DNA construct as claimed in claim 8, wherein said binding site is the sequence 5'-TTATCT-3'.

10. A DNA construct as claimed in claim 1, wherein said activator sequence is selected from the group consisting of the VEGF promoter, the VEGF enhancer, the cDNA encoding c-SRC, and the cDNA encoding v-SRC.

11. A DNA construct as claimed in claim 1, wherein said activator sequence is selected from the group consisting of the promoter for mouse mammary tumor virus and the promoter for a steroid receptor gene.

12. A DNA construct as claimed in claim 1, wherein said antitumor substance is selected from the group consisting of retinoblastoma protein p110, retinoblastoma protein p107, and retinoblastoma protein p130.

13. A DNA construct as claimed in claim 1, wherein said antitumor substance is protein p53.

14. A DNA construct as claimed in claim 1, wherein said antitumor substance is selected from the group consisting of a cycline-dependent kinase inhibitor, protein p21, and protein p16.

15. A DNA construct as claimed in claim 1, wherein said antitumor substance is GADD45 protein.

16. A DNA construct as claimed in claim 1, wherein said antitumor substance is bak protein.

17. A DNA construct as claimed in claim 1, wherein said antitumor substance is a protein which inhibits angiogenesis.

18. A DNA construct as claimed in claim 1, wherein said antitumor substance is a protein which exhibits a cytostatic effect.

19. A DNA construct as claimed in claim 1, wherein said antitumor substance is a protein which stimulates inflammation.

20. A DNA construct as claimed in claim 1, wherein said antitumor substance is an enzyme that cleaves a precursor of a cytostatic agent to produce a cytostatic agent.

21. A DNA construct as claimed in claim 12, wherein amino acids Thr-246, Thr-350, Ser-601, Ser-605, Ser-780, Ser-786, Ser-787, Ser-800, and Ser-804 of retinoblastoma protein p110, p107 or p130 are replaced with non-naturally occurring amino acids, and wherein said protein lacks phosphorylation sites, and wherein said protein is capable of binding the large T-antigen.

22. A DNA construct as claimed in claim 21, wherein amino acids Thr-246, Ser-601, Ser-605, Ser-780, Ser-786, Ser-787, and Ser-800 are replaced with Ala, and wherein Thr-350 is replaced with Arg and wherein Ser-804 is replaced with Glu.

23. A DNA construct as claimed in claim 13, wherein said protein p53 is lacking the C-terminal Ser-392.

24. A DNA construct as claimed in claim 1, wherein said antitumor substance is selected from the group consisting of plasminogen activator inhibitor 1, plasminogen activator inhibitor 2, plasminogen activator inhibitor 3, angiostatin, platelet factor 4, TIMP-1, TIMP-2, and TIMP-3.

25. A DNA construct as claimed in claim 1, wherein said antitumor substance is selected from the group consisting of perforin, granzyme, IL-2, IL-4, IL-12, an interferon, IFNα, IFNβ, IFNgamma, TNFα, TNFβ, oncostatin M, RANTES, MCAF, IL-8, MIP-1α, MIP-1β, NAP-2, IL-3, IL-5, LIF, IL-11, and IL-13.

26. A DNA construct as claimed in claim 1, wherein said antitumor substance is a fusion protein comprising an immunoglobulin Fc fragment.

27. A DNA construct as claimed in claim 1, wherein said antitumor substance is an enzyme selected from the group consisting of herpes simplex virus thymidine kinase, cytosine deaminase, varicella zoster virus thymidine kinase, nitroreductase, β-glucuronidase, carboxypeptidase, lactamase, pyroglutamate aminopeptidase, D-aminopeptidase, oxidase, peroxidase, phosphatase, hydroxynitrile lyase, protease, esterase or glycosidase.

28. A DNA construct as claimed in claim 27, wherein said β-glucuronidase is selected from the group consisting of human, plant and bacterial β-glucuronidases.

29. A DNA construct as claimed in claim 27, wherein said carboxypeptidase is a Pseudomonas carboxypeptidase.

30. A DNA construct as claimed in claim 27, wherein said lactamase is a Bacillus cereus lactamase.

31. A DNA construct as claimed in claim 27, wherein the amino acid sequence of said enzyme has been mutated so that the lysosomal storage of said enzyme has been decreased relative to storage of the non-mutated enzyme.

32. A DNA construct as claimed in claim 27, wherein the naturally occurring signal sequence of said enzyme is replaced with a heterologous signal sequence, and wherein said heterologous signal sequence increases the extracellular secretion of said enzyme.

33. A DNA construct as claimed in claim 1, wherein said construct encodes more than one antitumor substance, and wherein each DNA sequence encoding an antitumor substance is linked to another DNA sequence encoding an antitumor substance by a DNA sequence for an internal ribosome entry site.

34. A vector comprising a DNA construct as claimed in claim 1.

35. A vector as claimed in claim 34, wherein the vector is a virus.

36. A vector as claimed in claim 35, wherein the virus is selected from the group consisting of retrovirus, adenovirus, adeno-associated virus, herpes simplex virus and vaccinia virus.

37. A plasmid comprising a DNA construct as claimed in claim 1.

38. A colloidal dispersion system comprising a DNA construct as claimed in claim 1.

39. A system as claimed in claim 38, wherein the system comprises liposomes.

40. A system as claimed in claim 39, wherein said system comprises polylysine ligands.

41. A vector according to claim 34, further comprising a nucleotide sequence encoding a ligand which binds to a membrane structure of endothelial cells.

42. A vector as claimed in claim 41, wherein said ligand is selected from the group consisting of a polyclonal antibody, a monoclonal antibody, and an antibody fragment, and wherein the variable domains of said ligand bind to membrane structures of endothelial cells.

43. A vector as claimed in claim 41, wherein said ligand is selected from the group consisting of a cytokine, a growth factor, a fragment of a growth factor, a fragment of a cytokine, a constituent sequence of a growth factor, and a constituent sequence of a cytokine, and wherein said ligand binds to receptors on smooth muscle cells.

44. A vector as claimed in claim 41, wherein said ligand is selected from the group consisting of an adhesion molecule, SLeX, LFA-1, MAC-1, LECAM-1 and VLA-4.

45. A vector as claimed in claim 42, wherein said membrane structure is selected from the group consisting of a mannose receptor, IL-1, a growth factor, PDGF, FGF, VEGF, and TGFS.

46. A pharmaceutical preparation comprising a DNA construct as claimed in claim 1.

47. A pharmaceutical preparation as claimed in claim 46, wherein said preparation is suitable for intravenous administration.

48. A pharmaceutical preparation as claimed in claim 46, wherein said preparation is suitable for intraarterial administration.

49. A pharmaceutical preparation as claimed in claim 46, wherein said preparation is suitable for intracavity injection.

50. A pharmaceutical preparation as claimed in claim 46, wherein said preparation is suitable for injection into tissue.

51. A pharmaceutical preparation as claimed in claim 46, wherein said preparation is suitable for injection into gaps in tissue.

52. A pharmaceutical preparation as claimed in claim 46, wherein said preparation is suitable for local administration.

* * * * *